United States Patent [19]
Cargill et al.

[11] Patent Number: 5,609,826
[45] Date of Patent: Mar. 11, 1997

[54] METHODS AND APPARATUS FOR THE GENERATION OF CHEMICAL LIBRARIES

[75] Inventors: John Cargill, San Diego; Romaine R. Maiefski, Oceanside, both of Calif.

[73] Assignee: Ontogen Corporation, Carlsbad, Calif.

[21] Appl. No.: 422,869

[22] Filed: Apr. 17, 1995

[51] Int. Cl.$^6$ .................................................. B01L 11/00
[52] U.S. Cl. ............................ 422/99; 422/102; 422/101; 422/196
[58] Field of Search .............................. 422/102, 99, 63, 422/101, 196; 356/244, 246

[56] References Cited

U.S. PATENT DOCUMENTS

| | | | |
|---|---|---|---|
| 4,154,795 | 5/1979 | Thorne | 422/99 |
| 4,304,865 | 12/1981 | O'Brien et al. | 422/101 |
| 4,319,841 | 3/1982 | Suovaniemi et al. | 422/102 |
| 4,483,964 | 11/1984 | Urdea et al. | 536/25.5 |
| 4,517,338 | 5/1985 | Urdea et al. | 536/25.3 |
| 4,659,222 | 4/1987 | Ekholm | 356/244 |
| 4,746,490 | 5/1988 | Saneii | 422/62 |
| 4,797,259 | 1/1989 | Matkovich et al. | 422/101 |
| 4,948,442 | 8/1990 | Manns | 156/73.1 |
| 4,948,564 | 8/1990 | Root et al. | 422/101 |
| 4,970,165 | 11/1990 | Uhrin | 435/287 |
| 5,039,493 | 8/1991 | Oprandy | 422/101 |
| 5,048,957 | 9/1991 | Berthold et al. | 356/246 |
| 5,108,704 | 4/1992 | Bowers et al. | 422/101 |
| 5,219,528 | 6/1993 | Clark | 422/101 |
| 5,240,680 | 8/1993 | Zuckermann et al. | 422/67 |
| 5,252,296 | 10/1993 | Zuckermann et al. | 422/116 |
| 5,283,039 | 2/1994 | Aysta | 422/101 |
| 5,324,483 | 6/1994 | Cody et al. | 422/131 |
| 5,342,581 | 8/1994 | Sanadi | 422/101 |

FOREIGN PATENT DOCUMENTS

| | | | |
|---|---|---|---|
| WO93/12427 | 6/1993 | WIPO | G01N 33/68 |
| WO94/11388 | 5/1994 | WIPO | C07K 1/04 |

OTHER PUBLICATIONS

DeWitt, S. H., et al.; "Diversomers": An approach to non-peptide, nonoligomeric chemical diversity; Proc. Natl. Acad. Sci. USA, vol. 90, pp. 6909–6913, Aug. 1993.

*Primary Examiner*—Robert J. Warden
*Assistant Examiner*—Alexander Markoff
*Attorney, Agent, or Firm*—Pennie & Edmonds

[57] ABSTRACT

Methods and apparatus for the generation of chemical libraries are described. The preferred embodiments include a reaction block which uses replaceable reaction chambers supported in the block. Each reaction block is fitted with four sets of 12 reaction chambers, and has fittings that facilitate robotic manipulation. The reaction chambers are preferably fitted with a frit. An s-shaped trap tube snaps into a fitting on the bottom of each reaction chamber. The trap tube runs into a drain tube. The reaction block is fitted with gas (preferably $N_2$) lines and a septum seal such that gas pressurization empties the reaction chambers into the drain tubes. The drain tubes are arranged so as to mate directly with a standard 96 well microtiter plate for the collection of material. A docking station provides for secure registration of the reaction blocks, and provides for introduction of gases and liquids into the reaction blocks. An inert atmosphere in the reaction block is maintained by a top and (optional) bottom seal. A synthesis support may be introduced into each reaction chamber as a slurry, and the top septum fastened. A needle pipettes reagents from an array of reagent containers into the reaction chambers, and maintains the inert atmosphere. A locking reagent container rack keeps the containers securely in place.

76 Claims, 9 Drawing Sheets

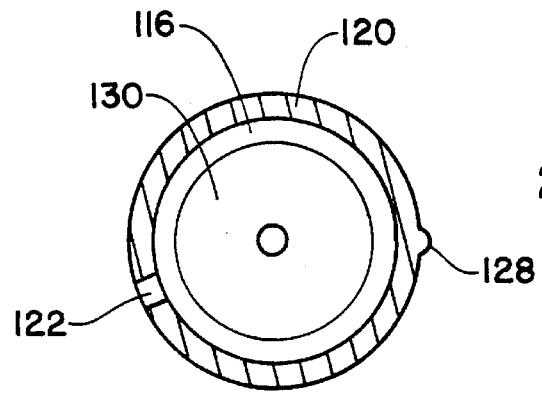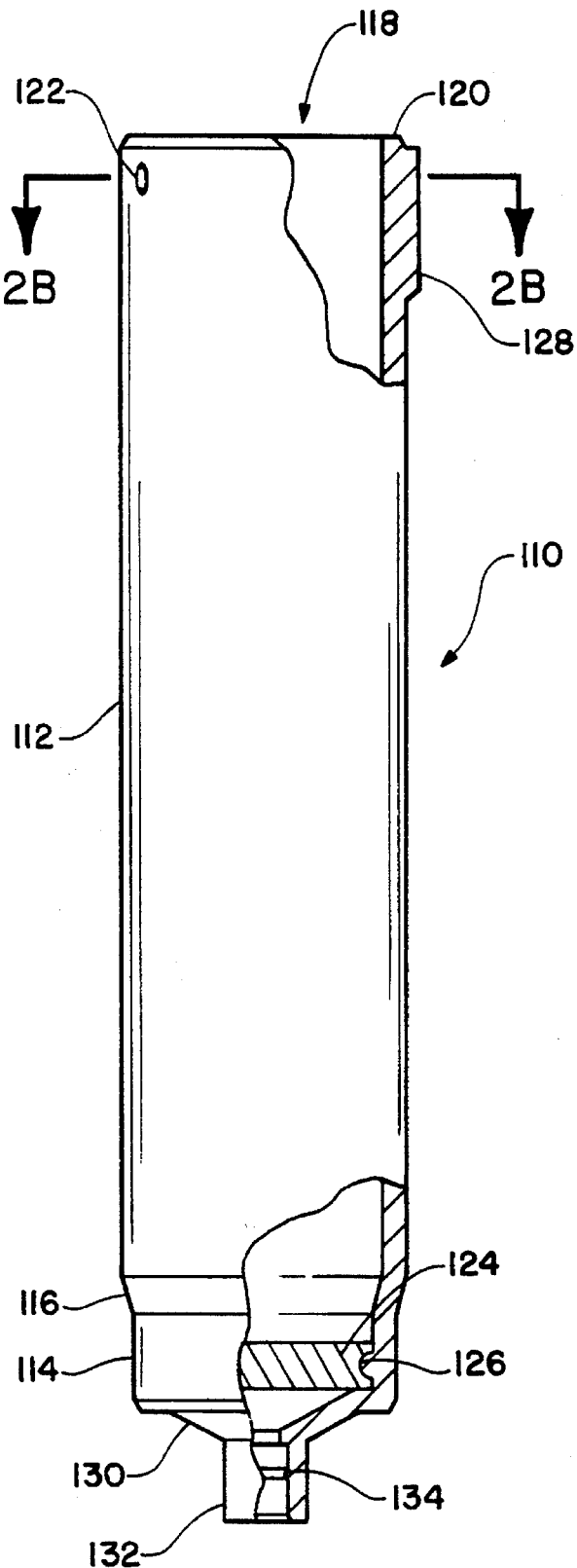
FIGURE 2B
FIGURE 3
FIGURE 2A

METHODS AND APPARATUS FOR THE GENERATION OF CHEMICAL LIBRARIES

FIELD OF THE INVENTION

The present invention relates generally to combinatorial synthesis, and more particularly to methods and apparatus for the generation of chemical libraries of known composition.

BACKGROUND

The relationship between structure and function of molecules is a fundamental issue in the study of biological and other chemistry-based systems. Structure-function relationships are important in understanding, for example, the function of enzymes, cellular communication, and cellular control and feedback mechanisms. Certain macromolecules are known to interact and bind to other molecules having a specific three-dimensional spatial and electronic distribution. Any macromolecule having such specificity can be considered a receptor, whether the macromolecule is an enzyme, a protein, a glycoprotein, an antibody, an oligonucleotide sequence of DNA, RNA or the like. The various molecules to which receptors bind are known as ligands.

Pharmaceutical drug discovery is one type of research that relies on the study of structure-function relationships. Much contemporary drug discovery involves discovering novel ligands with desirable patterns of specificity for biologically important receptors. Thus, the time necessary to bring new drugs to market could be greatly reduced through the use of methods and apparatus which allow rapid generation and screening of large numbers of ligands.

A common way to generate such ligands is to synthesize libraries of ligands on solid phase resins. Techniques for solid phase synthesis of peptides are described, for example, in Atherton and Sheppard, *Solid Phase Peptide Synthesis: A Practical Approach*, IRL Press at Oxford University Press, Oxford, England, 1989. Techniques for solid phase synthesis of oligonucleotides are described in, for example, Gait, *Oligonucleotide Synthesis: A Practical Approach*, IRL Press at Oxford University Press, Oxford, England, 1984. Each of these references is incorporated herein by reference.

Techniques for solution and solid phase multiple component combinatorial array syntheses strategies include U.S. patent application Ser. No. 08/092,862 filed Jan. 13, 1994, which is assigned to the assignee of the present invention, and which is incorporated herein by reference. Other synthetic strategies that may be employed are described in, for example, Bunin and Ellman, "A General and Expedient Method for the Solid Phase Synthesis of 1,4-Benzodiazepine Derivatives," *J. Amer. Chem. Soc.* 114:10997–10998 (1992); Bunin et al., "The Combinatorial Synthesis and Chemical and Biological Evaluation of a 1,4-Benzodiazepine Library," *Proc. Natl. Acad. Sci.* 91:4708–4712 (1994); U.S. Pat. No. 5,288,514 entitled "Solid Phase and Combinatorial Synthesis of Benzodiazepine Compounds on a Solid Support," issued Feb. 22, 1994; and PCT Publication WI 94/08051, Apr. 14 (1994), each of which is incorporated herein by reference.

Since the introduction of solid phase synthesis methods for peptides, oligonucleotides and other polynucleotides, new methods employing solid phase strategies have been developed that are capable of generating thousands, and in some cases even millions, of individual peptide or nucleic acid polymers using automated or manual techniques. These synthesis strategies, which generate families or libraries of compounds, are generally referred to as "combinatorial chemistry" or "combinatorial synthesis" strategies.

Combinatorial chemistry strategies can be a powerful tool for rapidly finding novel ligands to receptors of interest. To date, three general strategies for generating combinatorial libraries have emerged: "spatially-addressable," "split-bead," and "recombinant" strategies These methods differ in one or more of the following aspects: reaction vessel design, polymer type and composition, control of physical variables such as time, temperature and atmosphere, isolation of products, solid-phase or solution-phase methods of assay (i.e., chemical analysis), simple or complex mixtures, and methods for finding or determining the structure of the individual library members.

Of these general strategies, several sub-strategies have been developed. One spatially-addressable strategy that has emerged involves the generation of peptide libraries on immobilized pins that fit the dimensions of standard, 96 well microtiter plates. See PCT patent publication Nos. 91/17271 and 91/19818, each of which is incorporated herein by reference. This method has been used to identify peptides which mimic discontinuous epitopes, Geysen et al., "Screening Chemically Synthesized Peptide Libraries for Biologically Relevant Molecules," *Bioorg Med Chem. Lett.* 3: 397–404 (1993), and to generate benzodiazepine libraries, U.S. Pat. No. 5,288,514 entitled "Solid Phase and Combinatorial Synthesis of Benzodiazepine Compounds on a Solid Support," issued Feb. 22, 1994 and Bunin et al., "The Combinatorial Synthesis and Chemical and Biological Evaluation of a 1,4-Benzodiazepine Library," *Proc. Natl. Acad Sci.* 91:4708–4712 (1994). The structures of the individual library members can be determined by analyzing the pin location (in the microtiter plate) in conjunction with the sequence of reaction steps (called a "synthesis histogram") performed during the synthesis.

A second, related spatially-addressable strategy that has emerged involves solid-phase synthesis of polymers in individual reaction vessels, where the individual vessels are arranged into a single reaction unit. An illustrative example of such a reaction unit is a standard 96-well microtiter plate; the entire plate comprises the reaction unit and each well corresponds to a single reaction vessel. This approach is an extrapolation of traditional single-column solid-phase synthesis.

As is exemplified by the 96-well plate reaction unit, each reaction vessel is spatially defined by a two-dimensional matrix. Thus, the structures of individual library members can be determined by analyzing the sequence of reactions to which each well was subjected.

Another spatially-addressable strategy employs "teabags" (i.e., small, porous sacks) to hold synthesis resin. The reaction sequence to which each teabag is subject is recorded. This recorded reaction sequence determines the structure of the oligomer synthesized in each teabag. See for example, Lam et al., "A New Type of Synthetic Peptide Library for Identifying Ligand-Binding Activity," *Nature* 354:82–84 (1991), Houghton et al., "Generation and Use of Synthetic Peptide Combinatorial Libraries for Basic Research and Drug Discovery," *Nature* 354:84–86 (1991), and Jung et al., "Multiple Peptide Synthesis Methods and Their Applications," *Agnew. Chem. Int. Ed. Engl.* 31:367–383 (1992), each of which is incorporated herein by reference.

In another recent development, the techniques of photolithography, chemistry and biology have been combined to create large collections of oligomers and other compounds on the surface of a substrate. See U.S. Pat. No. 5,143,854 and PCT patent publication Nos. 90/15070 and 92/10092, each of which is incorporated herein by reference.

Recombinant methods for preparing collections of oligomers have also been developed. See PCT patent publication nos. 91/17271 and 91/19818, each of which is incorporated herein by reference. Using these methods, one can identify each oligomer in the library by determining the DNA coding sequences in a recombinant organism or phage. However, since the library members are generated in vivo (i.e., within the organism or phage), recombinant methods are limited to polymers whose synthesis can occur in the cell. Thus, these methods typically have been restricted to constructing peptide libraries.

A third general strategy that has emerged involves the use of "split-bead" combinatorial synthesis strategies. See Furka et al., "General Methods for Rapid Synthesis of Multicomponent Peptide Mixtures," *Int. J. Pept. Protein Res.* 37: 487–493, (1991) which is incorporated herein by reference. In this method, beads are apportioned into smaller groups. These smaller groups (called "aliquots") each contain a number of beads that is evenly divisible into the total number of beads. Each aliquot exposed to a monomer, and the beads are pooled together again. The beads are mixed, reapportioned into aliquots, and then exposed to a second monomer. The process is repeated until the desired library is generated.

A technique for synthesizing labelled combinatorial chemistry libraries is described in co-pending application Ser. No. 08/303,766, filed Feb. 2, 1995, entitled "Methods and Apparatus for Synthesizing Labeled Combinatorial Chemical Libraries," filed Feb. 2, 1995, assigned to the assignee of the present invention, and incorporated herein by reference. In a preferred embodiment of that invention, each synthesized compound is associated with a unique identifier tag. The identifier tag relates a signal to a detector upon excitation with electromagnetic radiation.

To aid in the generation of combinatorial chemical libraries, scientific instruments have been produced which automatically perform many or all of the steps required to generate such libraries. An example of an automated combinatorial chemical library synthesizer is the Model 396 MPS fully automated multiple peptide synthesizer, manufactured by Advanced ChemTech, Inc. ("ACT") of Louisville, Ky.

The Model 396 MPS is capable of generating up to 96 different peptides or other small molecules in a single run. The syntheses occur simultaneously, with one amino acid being added to each growing polypeptide chain before addition of the next successive amino acid to any polypeptide chain. Thus, each growing polypeptide chain contains the same number of amino acid residues at the end of each synthesis cycle.

The syntheses occur in an ACT proprietary plastic reaction block having 96 reaction chambers. While the ACT reaction blocks work for their intended purpose, they possess several shortcomings.

First, ACT reaction blocks are machined from a single piece of plastic. Thus, they require extremely intricate machining, and are quite expensive to manufacture. Furthermore, since ACT reaction blocks are in the form of a single unit, should a portion of a block become damaged or contaminated in some way, the entire reaction block would have to be discarded; there is no way to replace individual portions of an ACT block.

An additional drawback of the plastic ACT reaction blocks is that they cannot be efficiently heated or cooled to aid in chemical reactions that may require such heating or cooling.

Certain processes and chemistries require that the chemical reagents (which may be reactants, solvents, or reactants dissolved in solvents) be kept under an inert or anhydrous atmosphere to prevent reactive groups from reacting with molecular oxygen, water vapor, or other agents commonly found in air. Examples of atmosphere or moisture sensitive chemistries include peptide chemistry, nucleic acid chemistry, organometallic, heterocyclic, and chemistries commonly used to construct combinatorial chemistry libraries. Accordingly, such reagents must be stored and used under an anhydrous or inert atmosphere, such as one of argon, nitrogen, or other gases or mixtures of gases. Typically, containers of such reagents (and containers in which reactions using these reagents take place) are sealed from outside air by a gas impermeable septum. Reagents may be removed from or introduced into a septum sealed container via a non-coring pipetting needle that pierces the septum.

The composition of the septum depends on the chemistry involved, but common materials include thermoplastic rubber (TPR), natural rubber, teflon (typically used as a lining), and EPDM.

While the ACT reaction block can maintain an inert atmosphere when locked in place on the work station of the Model 396 MPS, there is no way to maintain an inert atmosphere once an ACT reaction block is removed from the work station. Thus, the reaction block must remain docked at the work station during the entire synthesis cycle. Since many reactants require several hours to react, this represents significant down time for the Model 396 MPS pipetting station, as it remains idle during the reaction period.

Additionally, creating an effective seal that maintains an inert atmosphere within the ACT reaction block is difficult due to the design of the block. To create such a seal, a top plate fitted with a rubber gasket is clamped onto the reaction chamber using six set screws. The screws are hand tightened to create the seal. The top of the block is machined such that a raised rim or bead separates the 96 reaction chambers into four sections of 24 reaction chambers each. Thus, individual chambers within a group of 24 are not sealed with a raised bead but rather sealed with a flat junction between the septa and the flat top of the machined polymeric reaction block. This design provides an inferior seal and allows solvent from the reaction chambers to cross contaminate reaction chambers within each group of 24 by creeping along the underside of the septa material or alternatively, by creeping along the gas passages machined into the top of the reaction block. Proper adjustment of the screws to distribute pressure evenly across each of the four sections (to create an effective seal) requires careful manipulation and cannot always be accomplished successfully.

A poorly formed seal can also create a problem with reagent cross-contamination. If the gasket does not seal evenly around each reaction chamber, reagents may seep from one reaction vessel into another.

While the ACT reaction block includes 96 reaction chambers, the compounds generated in the ACT reaction block cannot be directly transferred into a standard 96-well microtiter plate because the distance between the outlets of the reaction chambers is too great. For each reaction chamber to have the volume needed to perform reactions, the 96-reaction chamber ACT reaction block must necessarily be too large to mate with a standard 96-well microtiter plate. When reactions are complete, the user must transfer the contents of the reaction chambers into an array of 96 flat bottom glass vials supported in a plastic frame. The user must then manually pipette fluid from the glass vials into a microtiter plate for further analysis. This arrangement presents several disadvantages. First, the glass vials must be cleaned between uses, which increases the chance for contamination. Furthermore, the labor intensive nature of be the transfer increases a chance for error. Finally, this process cannot easily be automated.

The reagent delivery system of the Model 396 MPS also suffers limitations. While the septum-sealed reagent containers from which the reactants are drawn can be sealed under an inert or anhydrous atmosphere, the volume of reagent removed is not replaced with an equivalent or greater volume of inert gas. As reagents are withdrawn from the reagent containers, a partial vacuum is generated within the containers. If the pressure difference between the inside of the container and the external atmosphere is great enough, outside air may seep into the container through needle holes previously made in the septum.

The Model 396 MPS also employs a capacitance detector that can determine the fluid surface level in a reagent bottle. During operation of the Model 396 MPS, fluid is removed from reagent bottles by inserting a pipetting needle just below the fluid surface level such that reagent directly at the reagent-atmosphere interface is withdrawn. While this operation permits only the very tip of a pipetting needle to be contaminated, this operation may also result in the withdrawal of reagent that has been exposed to outside air.

Finally, the MPS detector described above can only operate if polar reagents are used. Thus, the Model 396 MPS may not be compatible with chemistries that utilize non-polar reagents.

Accordingly, there remains a need in the art for a relatively inexpensive, easy to manufacture reaction block having replaceable parts. There also remains a need in the art for a reaction block that can be efficiently heated and cooled, that can be moved from place to place while maintaining an inert atmosphere, and that can mate directly with a standard 96 well microtiter plate. An additional need that remains in the art is for a reaction block that easily and effectively seals each reaction chamber, and that reduces cross-contamination of reagents between reaction chambers. There also remains a need in the art for a reaction block that can be manipulated robotically.

There also remains a need in the art for a pipetting work station that can be operated to withdraw reagent from the bottom of a reagent bottle, away from the reagent-atmosphere interface, and that can be used with non-polar reagents.

There remains a further need in the art for a holder for septa sealed reagent bottles which prevents the movement of these bottles caused by friction between a pipetting needle and the septa seals.

SUMMARY

The preferred embodiments meet these needs by providing a reaction block which uses replaceable reaction chambers supported in the block. Each reaction block is fitted with four sets of 12 reaction chambers, and has fittings that facilitate robotic manipulation.

The reaction chambers are preferably fitted with a frit. An s-shaped trap tube snaps into a fitting on the bottom of each reaction chamber. The trap tube runs into a drain tube.

The reaction block is fitted with gas (preferably $N_2$) lines and a septum seal such that gas pressurization empties the reaction chambers into the drain tubes. The drain tubes are arranged so as to mate directly with a standard 96 well microtiter plate for the collection of material.

The reaction blocks preferably have high thermal stability and are preferably fitted with gas or liquid lines for heating or cooling.

A docking station provides for secure registration of the reaction blocks, and provides for introduction of gases and liquids into the reaction blocks. An inert atmosphere in the reaction block is maintained by a top and (optional) bottom seal. A synthesis support may be introduced as a slurry or powder through the fastened septa with a suitable septa-piercing needle assembly. Alternatively, a synthesis support may be introduced into each reaction chamber as a slurry or powder with the top removed and the top then fastened after addition. A needle pipettes reagents from an array of reagent containers into the reaction chambers, and maintains the inert atmosphere. A locking reagent container rack keeps the containers securely in place.

BRIEF DESCRIPTION OF THE DRAWINGS

FIGS. 2A. and 2B are a side and top view of a reaction chamber according to a preferred embodiment.

FIG. 3 is a side cross-sectional view of the reaction chamber shown in FIG. 2 further including a trap tube and drain tube.

DETAILED DESCRIPTION

Figure 1:
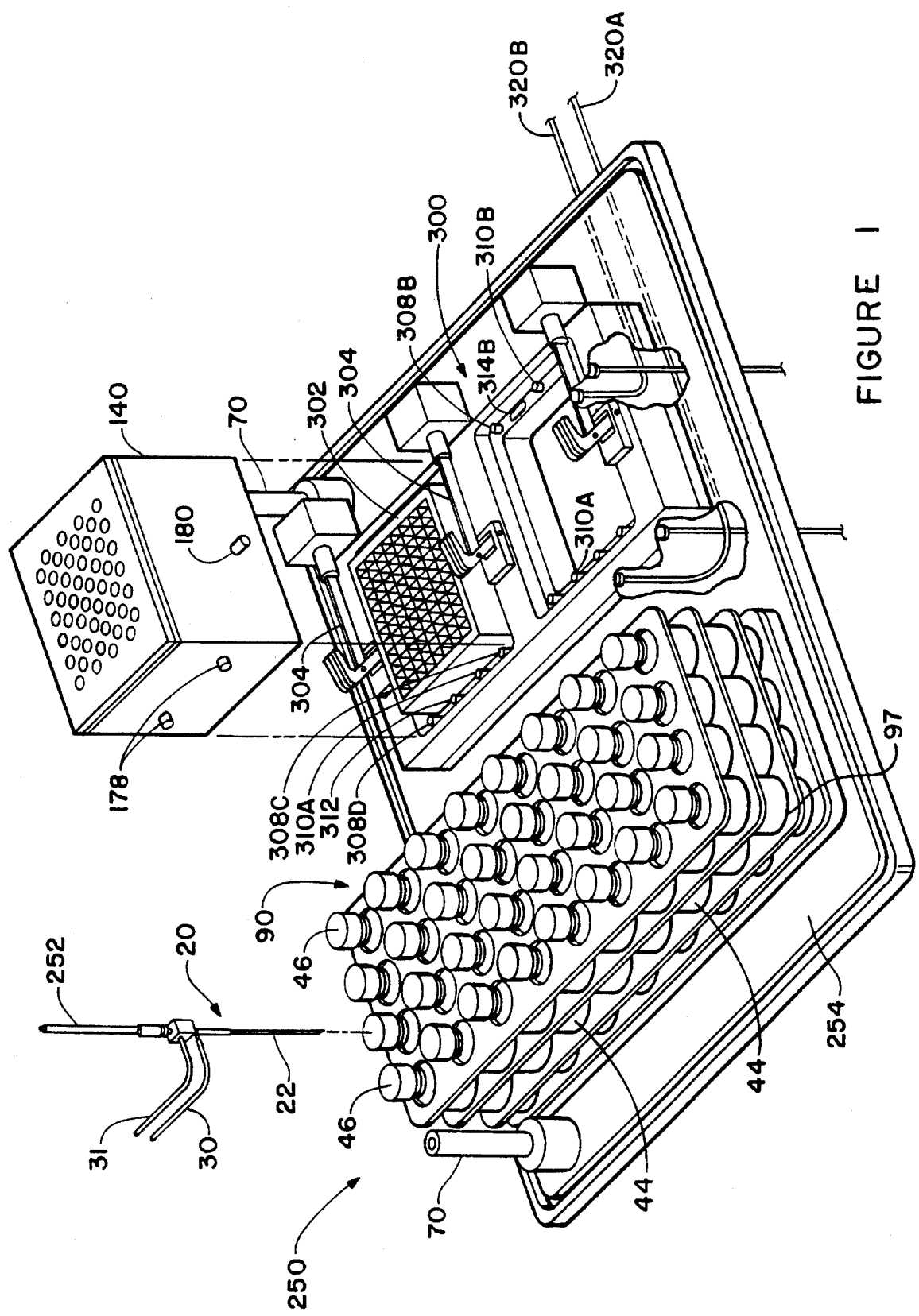
FIG. 1 is a plan view of a pipetting work station according to a preferred embodiment.

The structure and function of the preferred embodiments can best be understood by reference to the drawings. The reader will note that the same reference numerals appear in multiple figures. Where this is the case, the numerals refer to the same or corresponding structure in those figures.

GENERAL OPERATION

FIG. 1 is a plan view showing a portion of an automated pipetting work station 250 as may be used in a preferred embodiment. Automated pipetting work station 250 may be a TECAN 5032 automated pipetting work station (Manufactured by TECAN AG, Feldbachstrasse 80, CH-8634 Hombrechtikon, Switzerland) with one or more pipetting arms 252. Pipetting arm 252 attaches to needle assembly 20, which is preferably a coaxial needle assembly of the type disclosed in concurrently filed application Ser. No. 08/423,142 filed Apr. 17, 1995 (attorney docket no. 8140—010) entitled "Pipetting Needle for Fluid Transfer Under Inert Atmosphere Operations," assigned to the assignee of the present invention and incorporated herein by reference. Coaxial needle assembly 20 includes a needle a gas inlet port 30, and may also include an electrical connection 31. Work station 250 may also include pipetting needle rinse stations 70, preferably of the type disclosed in concurrently filed application Ser. No. 08/423,141, filed Apr. 17, 1995 (attorney docket no. 8140–011) entitled "Pipetting Needle Rinse Station" assigned to the assignee of the present invention, and incorporated herein by reference.

A locking reagent container rack 90 holds several containers 44 of reagents sealed from the outside air with septum seals 46. Rack 90 is preferably placed on the left side of work station deck 254. On the right side of work station deck 254 is a docking station 300 for receiving two reaction blocks 140. Each reaction block 140 contains an array of 48 reaction chambers 110 (see, e.g., FIG. 4). A standard 96 well microtiter plate 302 may be mounted below reaction block 140 when product is to be removed from reaction chambers 110.

REACTION CHAMBER

Referring now to FIG. 2, a reaction chamber 110 according to a preferred embodiment is shown. Reaction chamber 110 is preferably made of an injection molded or extruded polymer such as polypropylene, although polyethylene, teflon, glass, or any other inert material able to withstand the temperature, pressure, and chemical environment to which reaction chamber 110 is exposed could also be used. Reaction chamber 110 preferably also has an internal volume of approximately 2 ml.

Reaction chamber 110 includes a generally cylindrical body portion 112 of a first diameter, and a generally cylindrical lower body portion 114 that is coaxial with and of a smaller diameter than body portion 112. Body portion 112 is connected to generally cylindrical lower body portion 114 by frustum, or tapered section 116. Body portion 112 has a top opening 118 which preferably has a rounded top surface 120 to facilitate sealing against a septum. Body 112 has a gas input port 122 located below top surface 120. Gas input port 122 is positioned such that it will be located above the bottom of waste basin 160 of reaction block 140 (See FIGS. 4 and 5). As will be discussed below, this positioning will prevent possible cross-contamination of chemicals by blocking a direct flow path from port to port or from port to septum.

Reaction chamber 110 preferably also includes a keying protrusion 128. Keying protrusion 128 prevents reaction chamber 110 from being inserted into reaction block 140 unless it is in a predetermined orientation. This feature will be discussed further below.

Lower portion 114 of reaction chamber 110 can receive a frit 124, which preferably supports a quantity of a synthesis support such as solid phase resin (not shown). Frit 124 is preferably a 70 micron polyethylene frit, although other types of frits such as sintered glass, sintered metals, and sintered ceramics may be used depending on the type of chemistry to be performed.

Frit 124 is preferably press fit into lower portion 114. Lower portion 114 has a smaller diameter than that of body 112 to allow insertion of frit 124 into lower portion 114 without damaging the inside surfaces of body 112. Lower portion 114 preferably also includes an annular bead 126 to retain frit 124 when it is pressed into place.

Reaction chamber 110 also includes a funnel shaped portion 130 immediately below lower portion 114, and below frit 124. Funnel shaped portion 130 allows full area exposure to the underside of frit 124, to enhance the draining of liquids from reaction chamber 110.

Immediately below funnel portion 130 is a generally cylindrical drain tube 132. Drain tube 132 is coaxial with and of smaller diameter than lower body portion 114. Drain tube 132 includes an annular sealing bead 134 to create a seal against the outside of S-shaped trap tube 136 (see FIG. 3). This seal may be strengthened by welding (or otherwise fixing) S-shaped trap tube 136 to annular sealing bead 134.

The purpose of trap tube 136 is to prevent the loss of liquids from reaction chamber 110 (when reaction chamber 110 is not pressurized) by bringing the level of an outlet for liquid above the normal liquid level of reaction chamber 110. Trap tube 136 connects to a drain tube 138. When reaction chamber 110 is pressurized, liquid flows through trap tube 136 and out drain tube 138. As will be discussed below, drain tube 138 will be positioned so as to deposit liquid into a well of a standard 96-well microtiter plate.

Trap tube 136 and drain tube 138 are preferably made of an injection molded or extruded polymer such as polypropylene, although polyethylene, teflon, or any other inert material able to withstand the temperature, pressure, and chemical environment to which trap tube 136 and drain tube 138 are exposed could also be used.

REACTION BLOCK

Figure 4:
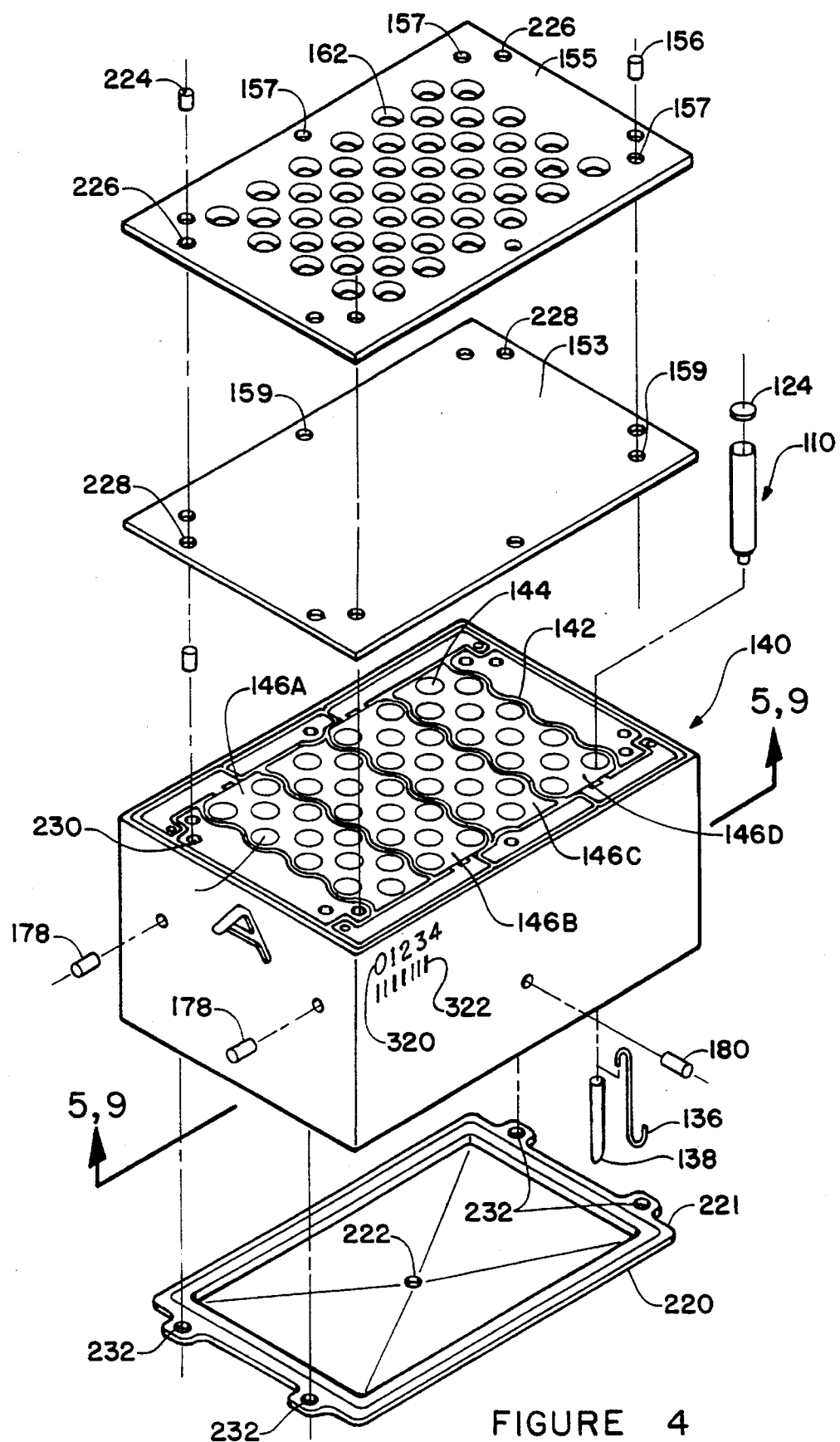
FIG. 4 Is an isometric view of a reaction block and its associated hardware according to a preferred embodiment.

Referring now to FIG. 4, an isometric view of a reaction block 140 (and its associated hardware) according to a preferred embodiment is shown. Reaction block 140 is preferably machined out of 6061 aluminum (which is easily machinable and has good corrosion resistance) and then anodized for additional corrosion protection. Reaction block 140 could also be hard coat anodized followed by teflon impregnation. Additionally reaction block 140 could be machined or molded from any suitable metal, engineering plastics, filled plastics, crystalline plastics, ceramics, machinable ceramics, or any other material that can withstand the temperature, pressure, and chemical environment to which reaction block 140 will be exposed. If non-metallic materials are used, product reaction could be enhanced by the application of microwaves. If materials transparent to ultraviolet (UV) light are used, product could be cleaved from the synthesis support using UV light, and without the application of an acid or base.

Each end of reaction block 140 is preferably fitted with two pins 178 to facilitate handling by a robotic gripper (not shown). Each side of reaction block 140 is preferably fitted with one pin 180 to facilitate securing reaction block 140 onto docking station 300. Robotic manipulation of reaction block 140 makes automation of the entire synthesis process possible. For example, reagents could be introduced into reaction chambers 110 when reaction block 140 is locked onto docking station 300 of pipetting work station 250. Reaction block 140 could then be moved to a separate docking station 300, vortexing shaker table, heating or cooling chamber, or any other location or device (not shown) useful in synthesis or the collection of material.

In a preferred embodiment, two types of reaction blocks capable of mating directly with a 96 well microtiter plate are contemplated: the 48 reaction chamber 110 (and drain tube 138) positions of a first type of (or "A") block are offset from the 48 reaction chamber and drain tube positions of a second type of (or "B") block such that a type "A" and a type "B" block can fill every position in a standard 96 well microtiter plate. The ability to deposit material directly into a 96-well microtiter plate eliminates the possible contamination and human error problems discussed above with respect to the ACT reaction block.

Reaction block 140 may be color coded for ease of identification, may have identification numbers 320 machined into or printed on the sides, and may also have a bar code 322 printed on the side for identification by machine.

Figure 5:
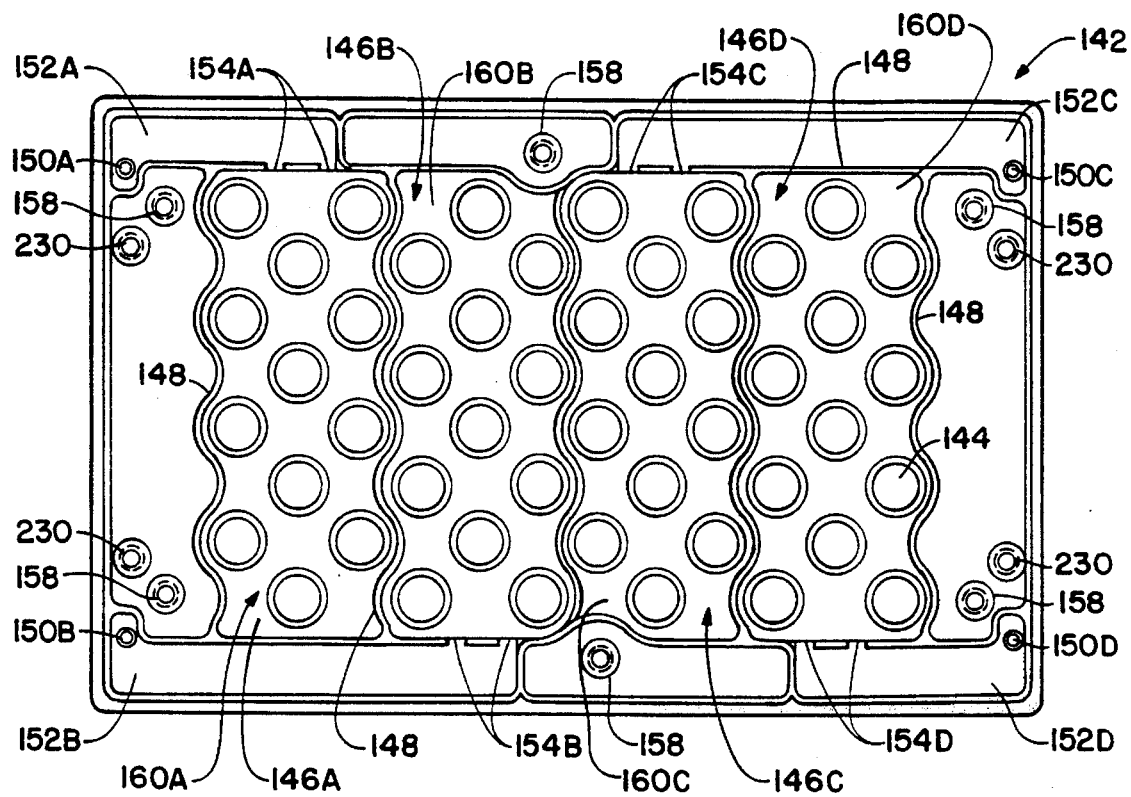
FIG. 5 is a top view of the reaction block shown in FIG. 4.

Referring now to FIG. 5, top portion 142 of reaction block 140 is shown. Top portion 142 preferably has an array of circular openings 144 arranged in a staggered grid. In a preferred embodiment, reaction block 140 has 48 circular openings 144. Openings 144 also preferably include a keying notch 145 (see FIG. 4) which cooperates with keying protrusion 128 on reaction chamber 110 and requires reaction chamber 110 to be in a predetermined orientation when inserted into opening 144.

The 48 openings 144 are divided into four chambers 146A through 146D of twelve openings 144 each. The chambers 146A–D are separated from each other by a plurality of raised beads 148, which are preferably machined into top portion 142.

Top portion 142 also includes four gas outlet ports 150A through 150D. Gas flows from gas outlet ports 150A–D, into gas inlet chambers 152A through 152D, respectively (which are defined by raised sealing beads 148). Gas then flows out through chamber exit ports 154A through 154D, respectively, and into chambers 146A through 146D, respectively. Gas flow to each chamber 146 can be individually controlled. For example, chambers 146A and 146C can be pressurized, without pressurizing chambers 146B and 146D.

When reaction chambers 110 are inserted and locked into place in openings 144, the top portions 120 of reaction chambers 110 are in approximately the same plane as the tops of raised sealing beads 148.

Top surfaces 120 of reaction chambers 110 and raised sealing beads 148 are sealed by a sheet of septum material 153 (See FIG. 4). Septum 153 is preferably manufactured from 1/10" thermoplastic rubber (TPR) sheet. Septum 153 is retained by a septum retainer plate 155, which is preferably fastened with six captive screw-type fasteners 156 which attach to openings 157. Fasteners 156 pass through openings 159 in septum 153, and screw into machined fastener openings 158.

Figure 7:
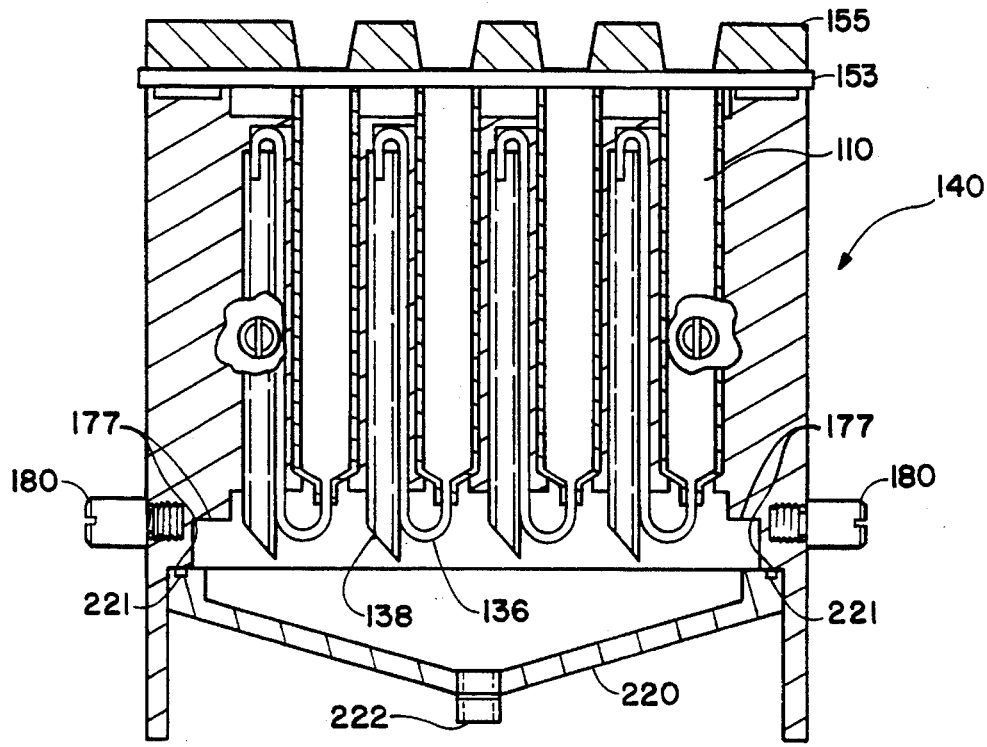
FIG. 7 is a side cross-sectional view of the reaction block shown in FIG. 4 including a removable bottom seal.

Reaction block 140 may be sealed from underneath with a bottom seal 220. An o-ring or quad ring 221 (see FIG. 7) may be used to ensure a gas-tight seal. Bottom seal 220 may include a one-way valve 222 to allow pressure regulation. Bottom seal 220 is preferably fitted to reaction block 140 with screw-type fasteners 224. As can be seen in FIG. 4, fasteners 224 pass through openings 226 in plate 155, through openings 228 in septum 153, through openings 228 in reaction block 140, and into openings 232 in bottom seal 220. Bottom seal 220 permits a desired atmosphere or pressure to be maintained within reaction block 140, allowing reaction block 140 to be moved from location to location (such as to a separate shaker table, not shown) without loss of such atmosphere or pressure. This can be especially useful in chemistries requiring long periods of time for reactions to take place. In these situations, such reactions can take place away from the pipetting work station, allowing the pipetting work station to be used for other purposes.

In a preferred embodiment, septum retainer plate 155 is machined from 6061 aluminum and anodized. 6061 aluminum is a non-ferrous aluminum alloy, the composition of which is defined according to the Aluminum Association Standardized System of Alloy Designation. Specifically, 6061 aluminum comprises aluminum alloyed with 0.25% copper, 0.6% silicon, 1.0% magnesium, and 0.25% chromium. A fuller description of the properties of this standardized aluminum alloy can be seen, for example, in "Machinery's Handbook", (19th edition; pp. 2164–2177) published by Industrial Press Inc., 200 Madison Ave., New York, N.Y. 10016. However, retainer plate 155 could also be machined or molded from engineering plastics, ceramics, or any other material that can withstand the temperature, pressure, and chemical environment to which retainer plate 155 will be exposed.

Plate 155 is also preferably machined with 48 openings 162 positionally matched with openings 144 of reaction block 140 (and thus with openings 118 of reaction chambers 110) to accurately control the compression of the septum 153 between the tops 120 of reaction chambers 110, and plate 155.

Chambers 146 A through D include recessed waste basins 160 A through D, respectively, which are machined into top portion 142 below the level of chamber exit ports 154A–D. This prevents a back flow of fluids from waste basins 160A–D into chamber exit ports 154A–D.

As discussed above, reaction chambers 110 and openings 144 are preferably "keyed" with keying protrusions 128 and keying notches 145, respectively. This prevents reaction chambers 110 from being inserted fully into openings 144 unless the reaction chambers are in a predetermined proper orientation. In a preferred embodiment, reaction chambers 110 are oriented such that gas inlet ports 122 face away from chamber exit ports 154A–D. This prevents back flow of liquids from reaction chambers 110 into the chamber exit ports 154A–D. In addition, gas inlet ports 122 of reaction chambers 110 are oriented such that a back flow of liquid from one reaction chamber 110 is prevented from spilling directly into the gas inlet port 122 of an adjoining reaction chamber 110.

Figure 6:
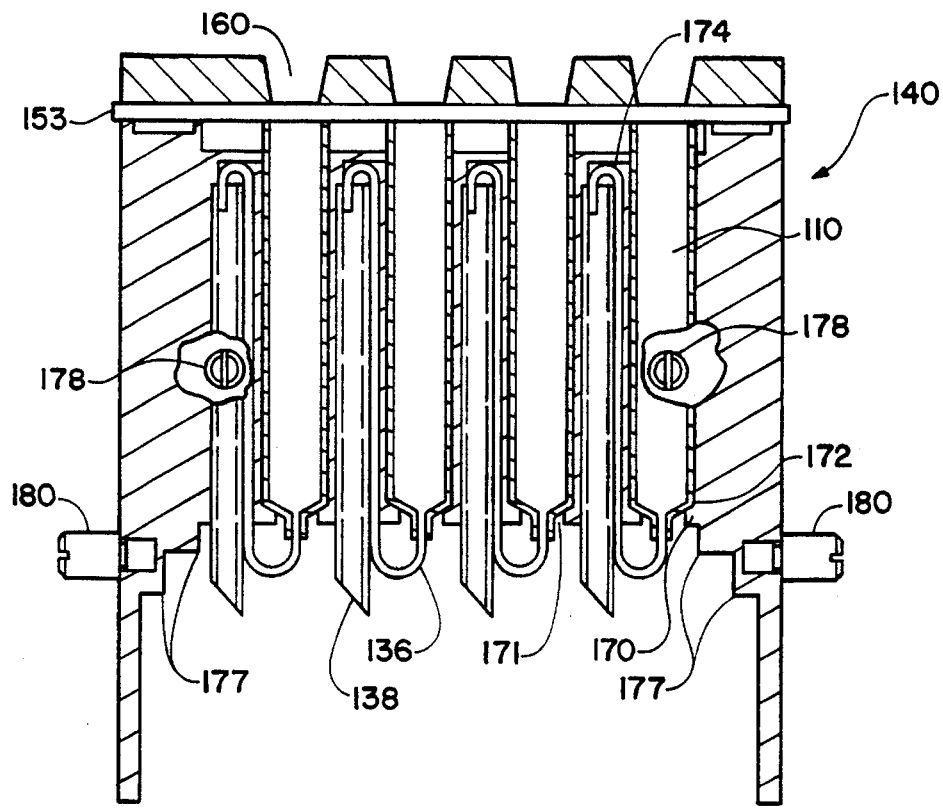
FIG. 6 is a side cross-sectional view of the reaction block shown in FIG. 4.

Referring now to FIG. 6, a side cross-sectional view of reaction block 140 is shown. Reaction chambers 110 are held in place by machined annular steps 170 (which define openings 171), and machined annular beads 172. S-shaped trap tube 136 and drain tube 138 are held in place by a friction fit against walls 174 and openings 176 (See FIGS. 9 and 10).

Figure 8:
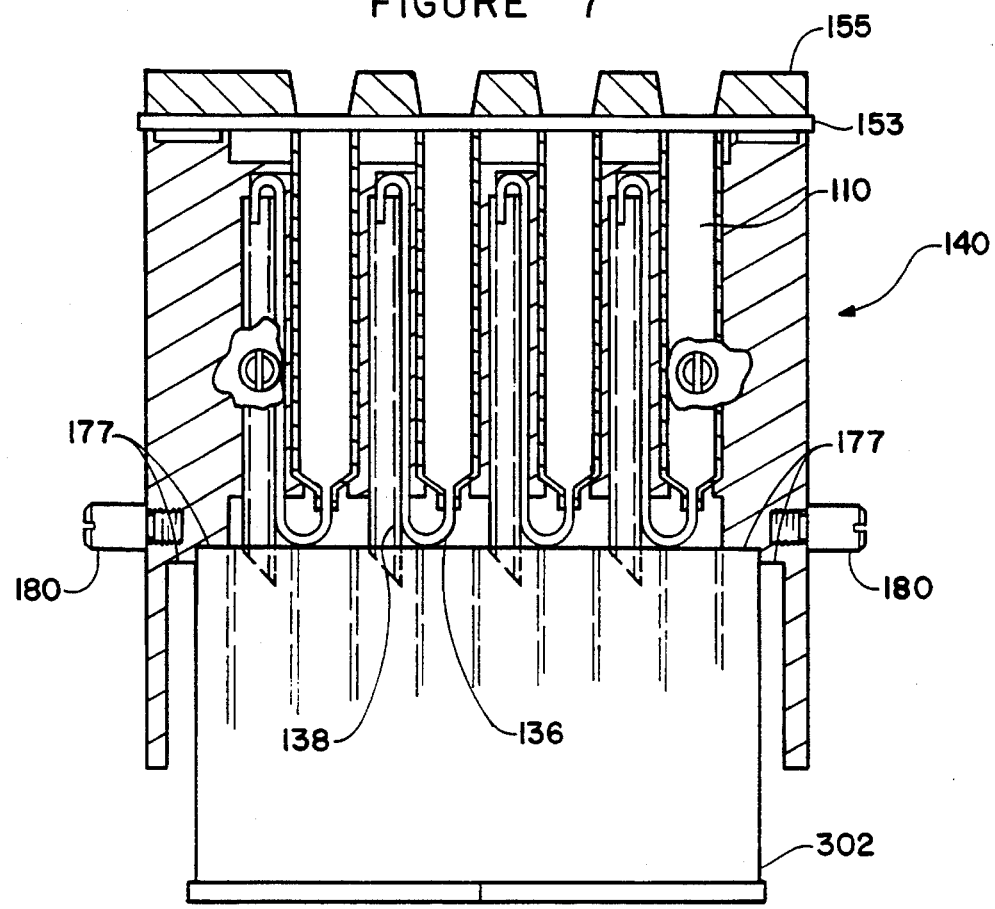
FIG. 8 is a side cross-sectional view of the reaction block shown in FIG. 4 including a microtiter plate.

Steps 177 are machined into the bottom of reaction block 140 to allow reaction block 140 to mate directly with a standard 96-well microtiter plate 302 (see, e.g., FIGS. 1 and 8). Steps 177 also allow mating and sealing with bottom seal 220 (see FIGS. 4 and 7).

Figure 9:
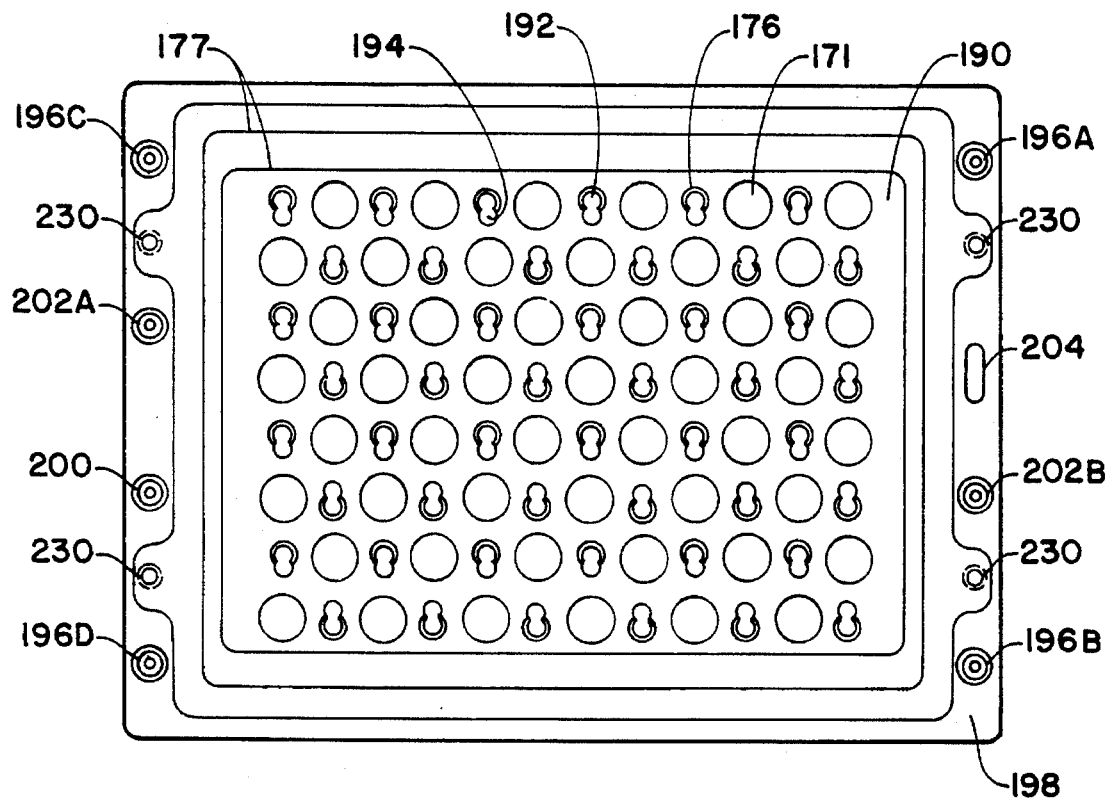
FIG. 9 is a bottom view of the reaction block shown in FIG. 4.
Figure 10B:
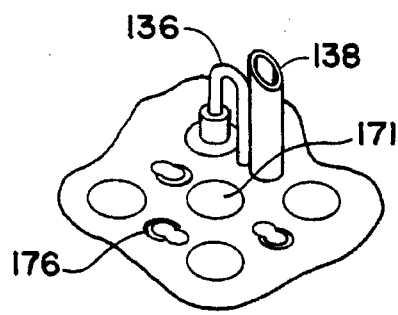
FIGS. 10A and 10B are both bottom plan views of the reaction block shown in FIG. 4.
Figure 10A:
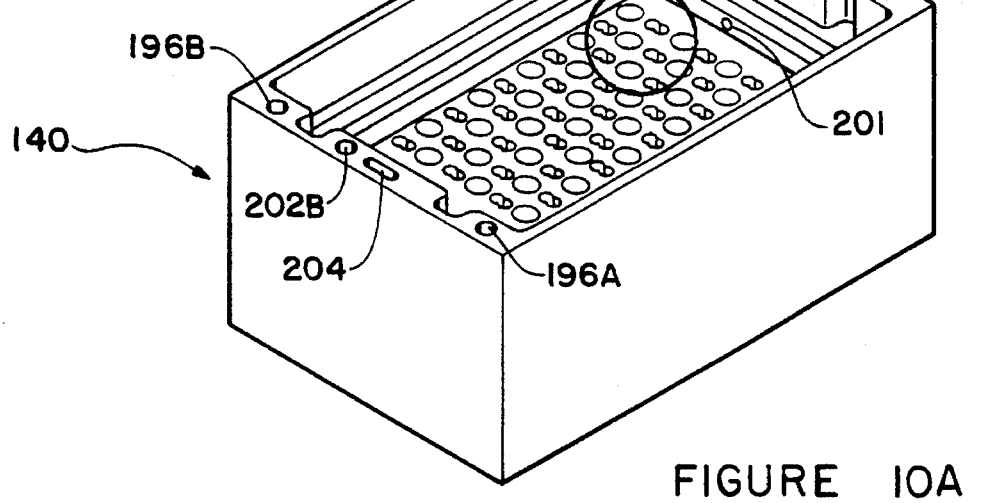

Referring now to FIGS. 9 and 10, plan and bottom views of reaction block 140 are shown. The underside of reaction block 140 includes a generally planar middle surface 190 which includes a plurality of openings 171 and 176, discussed above. Openings 176 include a relatively larger portion 192, which accommodates drain tube 138, and a relatively smaller portion 194, which accommodates s-shaped trap tube 136.

The underside of reaction block 140 also includes four gas inlet ports 196A through 196D located on bottom surface 198. Ports 196A–D connect to gas outlet ports 150A–D (See FIG. 5), respectively, through machined tunnels (not shown) in reaction block 140.

Also included on bottom surface 198 is a gas inlet port 200 which connects to a gas outlet port 201 via a machined tunnel (not shown). This allows pressure on the underside of reaction block 140 to be independently controlled when it is sealed by bottom seal 220 (see FIGS. 4 and 7).

Bottom surface 198 also includes two gas or liquid ports 202A and 202B. The interior of reaction block 140 is preferably machined to include passages (not shown) in which heating or cooling gas or liquid can flow if desired. Gas or liquid can enter port 202A and exit through port 202B, or vice versa. If reaction block 140 is made of material having high thermal stability or thermal mass such as 6061 aluminum, this arrangement allows reaction block 140 to be quickly and efficiently heated or cooled for chemistries that require such heating or cooling.

Figure 13:
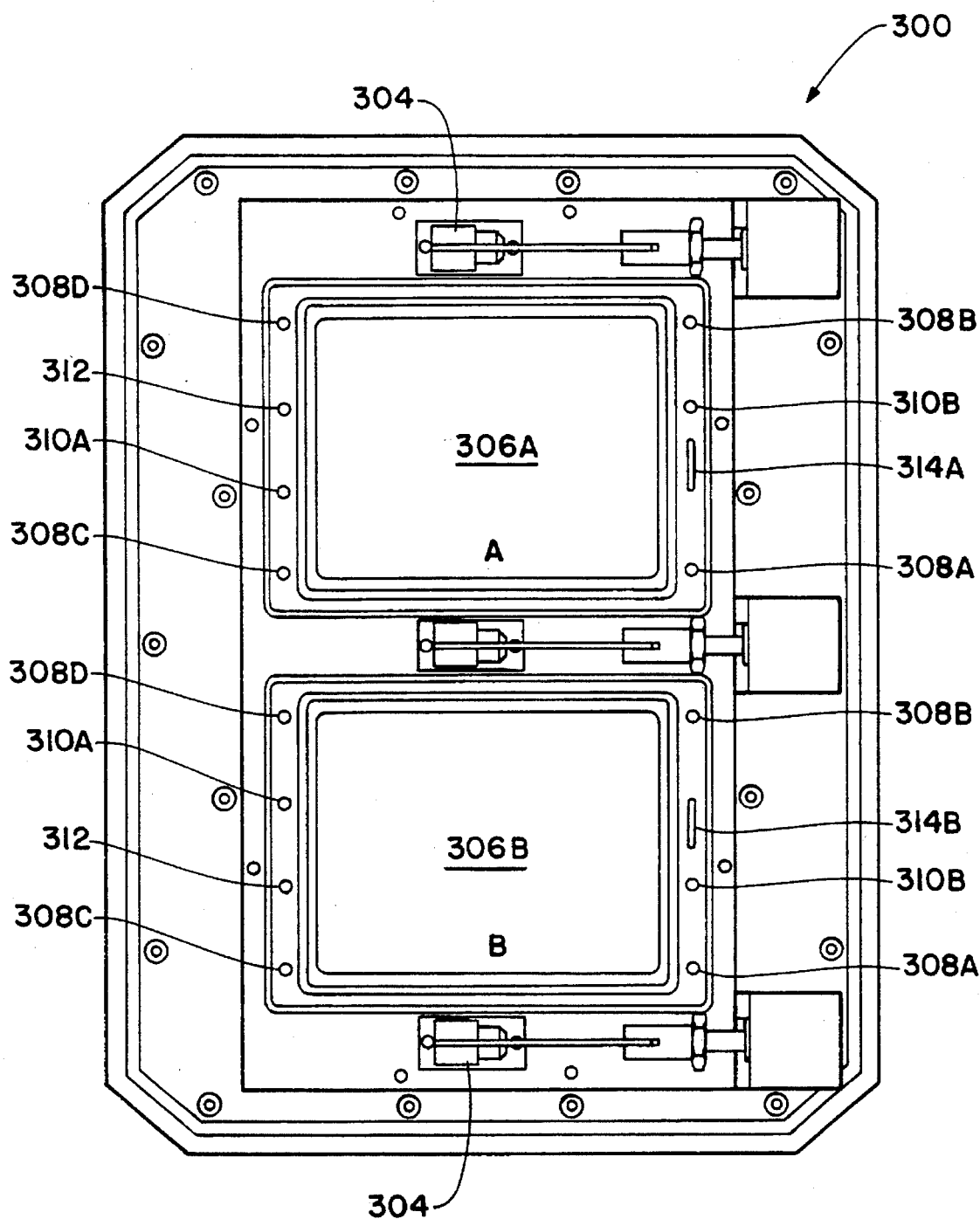
FIG. 13 is a top view of a docking station according to a preferred embodiment.

Ports 196A–D, 200 and 202 may also serve as guide pin holes to position reaction block 140 properly on docking station 300 (see FIGS. 1 and 13).

Finally, a bar magnet 204 may be mounted flush with surface 198. Bar magnet 204 serves to activate magnetic reed switch 314 mounted in docking station 300 (see FIG. 13). As will be discussed below, one or more reed switches prevent the operation of work station 250 unless one or more reaction blocks 140 are properly in place.

DOCKING STATION

Figure 14:
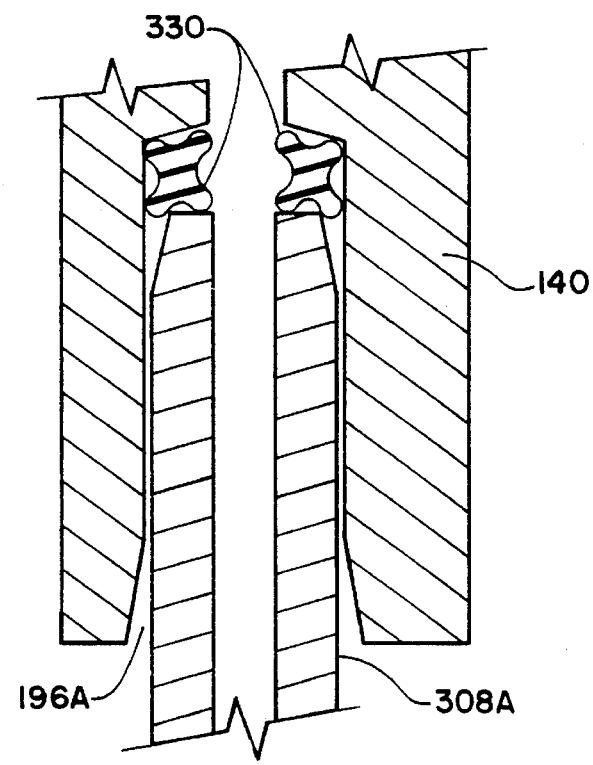
FIG. 14 is a cross sectional view of a connector in the docking station shown in FIG. 13, inserted into a port in the reaction block shown in FIG. 4.

Referring now to FIGS. 1, 13 and 14, a docking station 300 according to a preferred embodiment is shown. Docking station 300 preferably includes two stations, 306A and 306B, for receiving reaction blocks 140 of Type "A" and Type "B", respectively, as discussed above. As is known to those skilled in the art, docking station 300 may also be fitted with the proper motor, gears, and other elements (not shown) necessary for docking station 300 to act as a vortexing shaker, and preferably as a vortexing shaker having a fixed displacement and variable speed.

Docking station 300 also preferably includes three locking linkages 304 for locking onto pins 180 on reaction blocks 140. Each station 306 includes gas outlet connectors 308A through 308D which connect to ports 196A through 196D, respectively in reaction block 140 (see FIG. 9). Each station 306 also includes two coolant or heating fluid (i.e., gas or liquid) connectors 310A and 310B. FIG. 1 shown fluid lines 320A and 320B attached to connectors 310A and 310B, respectively. Although not shown in FIGS. 1 and 13, independently controllable fluid lines attach to each connector shown in docking station 300. Connectors 310A and 310B connect to ports 202A and 202B, respectively in reaction block 140 (See FIG. 9). A gas outlet connector 312 which connects to gas inlet port 200 of reaction block 140 is also included in each station 306.

Finally, stations 306A and 306B each include a magnetic reed switch 314A and 314B, respectively, which senses the presence of magnet 204 on reaction block 140. Station 306A, and more specifically the placement of port 312, is arranged such that only an A-type reaction block 140 can be fully inserted and locked into position. Similarly, station 306B, and more specifically the placement of port 312, is arranged such that only a B-type reaction block 140 can be fully inserted and locked into position.

Referring now to FIG. 14, a cross sectional view of a connector 308A inserted into port 196A of reaction block 140 is shown. Although only the interface between connector 308A and 196A will be discussed, it will be understood that similar interfaces are preferably included in other connections between reaction block 140 and docking station 300. In a preferred embodiment, connector 308A is inserted into port 196A. In this fashion, connector 308A acts as a guide pin to ensure proper alignment of reaction block 140 with station 306A. A gas-tight seal between connector 308A and port 196A is preferably provided by quad ring 330. A quad ring is preferred over a standard o-ring because a quad ring has less tendency to adhere to surfaces when connector 308A is removed from port 196A.

Figures 15, 16:
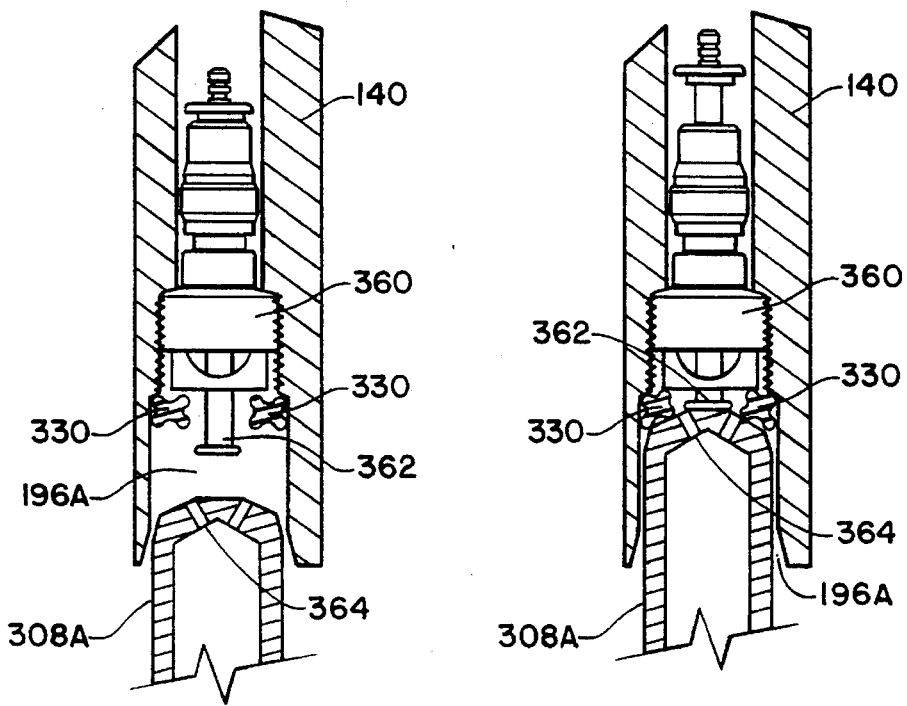
FIG. 15 is a cross sectional view of a connector in the docking station shown in FIG. 13, inserted into a port having a open valve in the reaction block shown in FIG. 4.
FIG. 16 is a cross sectional view of a connector in the docking station shown in FIG. 13, inserted into a port having a closed valve in the reaction block shown in FIG. 4.

Referring now to FIGS. 15 and 16 an alternative embodiment of port 196A is shown. In operations where inert or other atmosphere must be maintained, a normally closed valve, such as schraeder valve 360 may be placed in port 196A. Schraeder valve 360 may be replaced with a bi-directional elastomeric valve. In operation, connector 308A is inserted into port 196A and engages pin 362 of schraeder valve 360. Connector 308A also forms a seal against quad ring 330. Gas flows out of opening 364 and through schraeder valve 360.

When connector 308A is removed from port 196A, pin 362 of schraeder valve 360 moves downward, creating a gas-tight seal. Again, this allows reaction block 140 to be moved from place to place while maintaining a desired atmosphere.

Pipetting work station 250 (see FIG. 1) is preferably constructed such that operation of the work station cannot take place unless magnetic reed switches 314A and 314B detect the presence of one or both reaction blocks 140. That is, pipetting work station 250 will not operate unless reaction blocks 140 are properly mounted in stations 306A and 306B.

LOCKING REAGENT CONTAINER RACK

Figure 11:
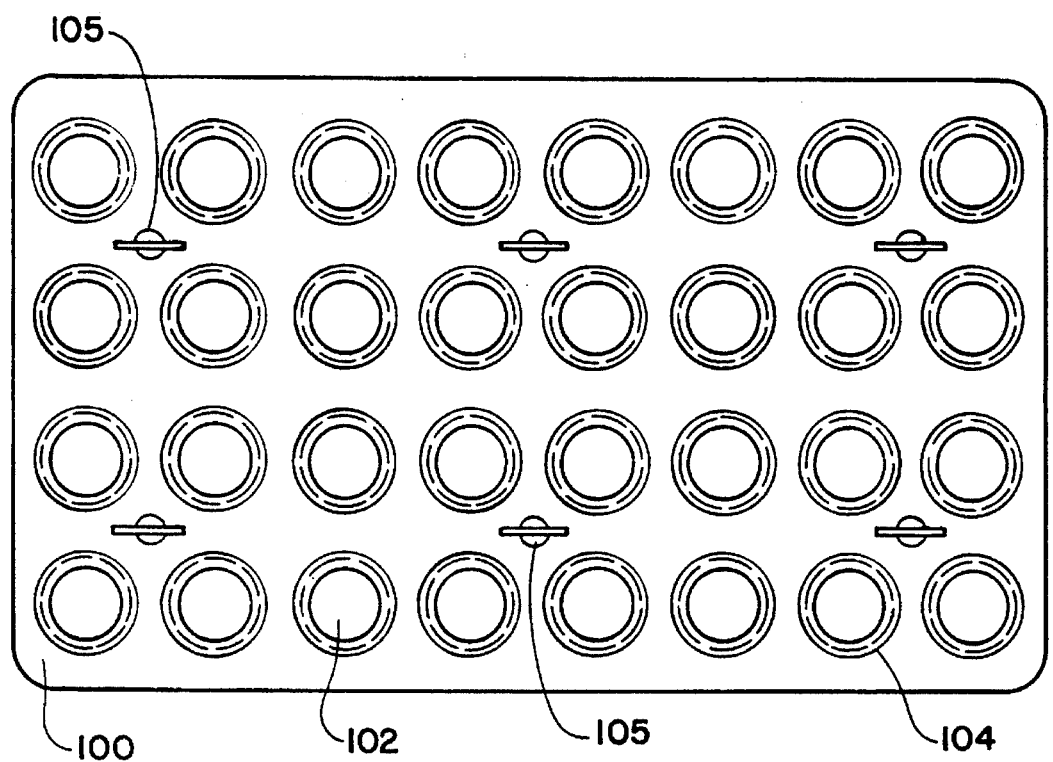
FIG. 11 is a top view of a locking reagent container rack according to a preferred embodiment.
Figure 12:
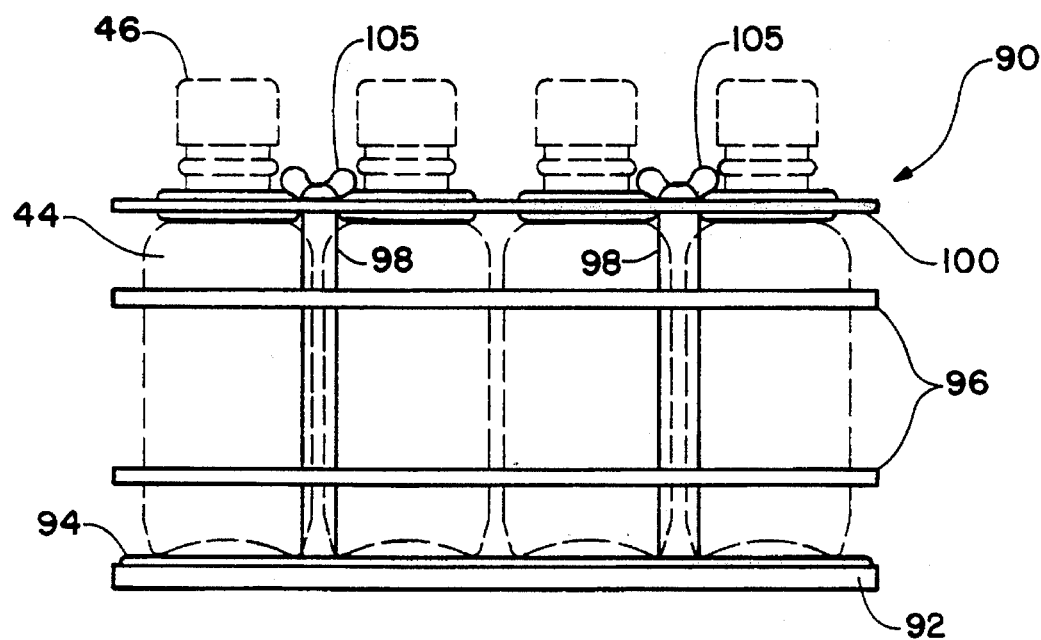
FIG. 12 is a side view of the locking reagent container rack shown in FIG. 11.

As was discussed above, pipetting reagents under inert atmosphere is often essential during the synthesis of combinatorial libraries. However, when pipetting reagents from a relatively lightweight septum-sealed container, the friction between the pipetting needle and the septum may be enough to lift the container from its resting position. This is obviously not desirable, as movement of and damage to the container and other equipment may result. Referring now to FIGS. 1, 11, and 12, a preferred embodiment of a locking reagent container rack 90 for pipetting under inert atmosphere is shown. Rack 90 includes a bottom plate or grating 92, preferably coated with a layer of rubber or soft material 94. Rack 90 may include one or more horizontal support plates 96, and includes a plurality of vertical support members 98. Horizontal plates 96 preferably include 48 circular openings 97 into which the containers 44 can be inserted. Rack 90 is preferably arranged such that septumsealed containers 44 can be arranged in a 4×8 array.

A top plate 100 rests on top of vertical support members 98 and snugly against containers 44. Top plate 100 preferably includes 48 circular openings 102 into which the tops of containers 44 can be inserted. Each opening 102 is preferably encircled with a rubber ring 104 to protect containers 44.

Plate 100 also includes one or more fasteners (such as quarter turn wing-nut type fasteners) 105 which fasten plate 100 to vertical support members 98, thus keeping containers 44 in place. Locking rack 90 may itself be fastened to a work surface (such as work station deck 254), although the weight of rack 90 and containers 44 would probably be sufficient to prevent any motion caused by friction between a pipetting needle and a septum.

EXAMPLE OF OPERATION

The many features of the preferred embodiments described above facilitate the relatively quick and efficient generation of chemical libraries. In the following discussion, a synthesis operation involving a type "A" reaction block 140 will be discussed. However, it will be understood that the following discussion will apply equally for a type "B" block as well.

In a typical operation, a synthesis support such as solid phase resin is deposited onto each frit 124 in reaction chambers 110. Reaction block 140 is then assembled as shown in FIG. 4. Bottom seal 220 may be mounted if reaction block 140 must be moved from place to place while maintaining a desired atmosphere or pressure.

Reaction block 140 may then be manually or robotically inserted into station 306A of docking station 300 on work station 250 (see FIGS. 1 and 13). At this point, microtiter plate 302 is not located in station 306A. Locking linkages 304 then grip pins 180, locking reaction block into place. A type "B" reaction block may be simultaneously mounted in station 306B.

Pipetting work station 250 then operates under computer control to deliver the chosen combination of reagents into reaction chambers 110. Specifically, pipetting needle 22 (as controlled by pipetting arm 252) is used to transfer reagents from septum 46 sealed containers 44 into septum 253 sealed reaction chambers 110. The interior and exterior of pipetting needle 22 may be cleaned as necessary in rinse stations 70. At any time that reaction block 140 is mounted in station 3069, reaction block 140 may be heated or cooled, pressurized with inert gas, or vortexed as described above.

For reactions that take a considerable amount of time, reaction block 140 may be manually or robotically moved to another docking station 300, or to some other location while the reactions are taking place. After the synthesis of the desired products has been completed, the products may be cleaved from the synthesis supports using the appropriate reagents. These reagents may be applied at work station 250, or they may be applied robotically at some other location. If bottom seal 220 had been mounted, it is then removed, and reaction block 140 is mounted onto a microtiter plate 302 in station 3069. Reaction chambers 110 are then pressurized, forcing the product out drain tubes 138 and into alternate wells of microtiter plate 302. Microtiter plate 302 is then moved to station 306B. A type "B" reaction block 140 is mounted on microtiter plate 302, and product is then deposited into the alternate empty wells of microtiter plate 302 as discussed above. Again, this process allows product to be deposited directly into the wells of a standard microtiter plate, without requiring an intermediate step.

The present invention has been described in terms of a preferred embodiment. The invention, however, is not limited to the embodiment depicted and described. Rather, the scope of the invention is defined by the appended claims.

What is claimed is:

1. A reaction block comprising:
   a plurality of reaction chambers;
   a first side wall and a second side wall, the first and second side walls having a first width and a first height;
   a first end wall and a second end wall, the first and second end walls having a second width narrower than the first width, and the first height;
   a first top surface bordered by the first and second side walls and the first and second end walls, the first top surface having:
      a plurality of generally circular openings for removably receiving the reaction chambers, the reaction chambers each having a circular opening and a second top surface;
      a gas port; and
      a plurality of raised beads defining the edges of a plurality of chambers;
      the raised beads having a third top surface which is in approximately the same plane as the second top surface of the reaction chambers;
   a flexible septum which seals against the second and third respective top surfaces of the reaction chambers and the raised beads; and
   a retainer plate which covers the septum.

2. A reaction block as in claim 1 wherein the retainer plate has a plurality of openings which spatially correspond to the openings of the reaction chambers.

3. A reaction block as in claim 2 wherein the retainer plate is held securely against the septum and the reaction block with a plurality of fasteners.

4. A reaction block as in claim 1 wherein the first top surface includes a first, a second, a third, and a fourth, separately controllable gas outlet ports, and wherein the raised beads define a first, a second, a third, and a fourth pressurization chambers. chambers.

5. A reaction block as in claim 4 wherein each pressurization chamber includes an equal number of the reaction chambers.

6. A reaction block as in claim 4 wherein each pressurization chamber includes 12 reaction chambers.

7. A reaction block as in claim 4 wherein the first, second, third, and fourth separately controllable gas outlet ports are in communication with the first, second, third, and fourth pressurization chambers, respectively.

8. A reaction block as in claim 5 wherein each of the pressurization chambers includes a waste basin which is recessed below the level of the second top surfaces of the reaction chambers.

9. A reaction block as in claim 8 wherein each of the four pressurization chambers has 12 of the reaction chambers.

10. A reaction block as in claim 1 wherein each of the generally circular openings on the first top surface have a keying notch, and wherein each of the reaction chambers have a keying protrusion.

11. A reaction block as in claim 1 wherein the block is made of aluminum.

12. A reaction block as in claim 11 wherein the block is made of 6061 aluminum.

13. A reaction block as in claim 11 wherein the aluminum has been anodized.

14. A reaction block as in claim 1 wherein the block is color coded.

15. A reaction block as in claim 1 wherein the block has an identification number.

16. A reaction block as in claim 1 wherein the septum is made from thermoplastic rubber.

17. A reaction block as in claim 16 wherein the septum is die cut with six registration holes and four access holes.

18. A reaction block as in claim 1 wherein the first and second side walls are fitted with one pin each to facilitate securing the block to a work station.

19. A reaction block as in claim 1 wherein the first and second end walls are fitted with two pins each to facilitate handling by a robotic gripper.

20. A reaction block as in claim 7 further including a bottom surface defined by the bottom edges of the first and second side walls and the first and second end walls, the bottom surface being parallel to the first top surface.

21. A reaction block as in claim 20 further including a first, second, third and fourth gas inlet ports in communication with the first, second, third, and fourth gas outlet ports of the first top surface, respectively.

22. A reaction block as in claim 21 wherein the first, second, third and fourth gas inlet ports are in the bottom surface.

23. A reaction block as in claim 22 further including an input port for receiving heating or cooling fluid.

24. A reaction block as in claim 23 wherein the input port for receiving heating or cooling fluid is in the bottom surface.

25. A reaction block as in claim 23 further including an output port for draining heating or cooling fluid.

26. A reaction block as in claim 25 wherein the output port for draining heating or cooling fluid is on the bottom surface.

27. A reaction block as in claim 26 further including a plurality of passages connecting the input port of receiving heating or cooling fluid to the output port for draining heating or cooling fluid.

28. A reaction block as in claim 20 wherein the bottom surface includes a magnet.

29. A reaction block as in claim 28 wherein the magnet is a bar magnet.

30. A reaction block as in claim 20 wherein each of the reaction chambers includes a drain tube.

31. A reaction block as in claim 30 further including a cavity extending upwardly from the bottom surface to a middle surface, the middle surface parallel to the first top surface and the bottom surface.

32. A reaction block as in claim 31 wherein the middle surface has openings for receiving the drain tubes.

33. A reaction block as in claim 32 wherein the cavity includes a machined step to facilitate mating with a microtiter plate.

34. A reaction block as in claim 33 wherein the cavity includes a second machined step to facilitate mating with a bottom seal.

35. A reaction block as in claim 34 wherein the bottom seal includes an o-ring which seals against the second machined step.

36. A reaction block as in claim 34 wherein the bottom seal includes a one-way pressure valve.

37. A reaction block as in claim 22 wherein the first, second, third and fourth gas inlet ports include a quad ring seal.

38. A reaction block as in claim 21 wherein the first, second, third and fourth gas inlet ports include a valve.

39. A reaction block as in claim 38 wherein the valve is a schraeder valve.

40. A reaction block as in claim 38 wherein the valve is a bi-directional elastomeric valve.

41. A reaction block comprising:

a plurality of reaction chambers;

a first side wall and a second side wall, the first and second side walls having a first width and a first height;

a first end wall and a second end wall, the first and second end walls having a second width narrower than the first width, and the first height;

a first top surface bordered by the first and second side walls and the first and second end walls, the top surface having:

a plurality of generally circular openings for removably receiving the reaction chambers, the reaction chambers each having a circular opening and a second top surface;

a gas port; and a plurality of raised beads defining the edges of a plurality of chambers;

the raised beads having a first top surface which is in approximately the same plane as the second top surface of the reaction chambers;

means for sealing against the second and third respective top surfaces of the reaction chambers and the raised beads; and a retainer plate which covers the means for sealing.

42. A reaction block as in claim 41 wherein the retainer plate has a plurality of openings which spatially correspond to the openings of the reaction chambers.

43. A reaction block as in claim 42 further including means for fastening the retainer plate to the means for sealing the reaction block.

44. A reaction block as in claim 41 wherein the first top surface includes a first, a second, a third, and a fourth, separately controllable gas outlet ports, and wherein the raised beads define a first, a second, a third, and a fourth pressurization chambers.

45. A reaction block as in claim 44 wherein each of the four pressurization chambers includes an equal number of the reaction chambers.

46. A reaction block as in claim 45 wherein the first, second, third, and fourth separately controllable gas outlet ports are in communication with the first, second, third, and fourth pressurization chambers, respectively.

47. A reaction block as in claim 45 wherein each of the four pressurization chambers includes a waste basin which is recessed below the level of the top surfaces of the reaction chambers.

48. A reaction block as in claim 45 wherein each of the four chambers has 12 of the reaction chambers.

49. A reaction block as in claim 41 wherein each of the generally circular openings on the first top surface have a keying notch, and wherein each of the reaction chambers have a keying protrusion.

50. A reaction block as in claim 41 wherein the block is made of aluminum.

51. A reaction block as in claim 50 wherein the block is made of 6061 aluminum.

52. A reaction block as in claim 50 wherein the aluminum has been anodized.

53. A reaction block as in claim 41 wherein the block is color coded.

54. A reaction block as in claim 41 wherein the block has an identification number.

55. A reaction block as in claim 41 wherein the block has a bar code.

56. A reaction block as in claim 41 wherein the first and second side walls are fitted with one pin each to facilitate securing the block to a work station.

57. A reaction block as in claim 41 wherein the first and second end walls are fitted with two pins each to facilitate handling by a robotic gripper.

58. A reaction block as in claim 46 further including a bottom surface defined by the bottom edges of the first and second side walls and the first and second end walls, the bottom surface being parallel to the first top surface.

59. A reaction block as in claim 58 further including a first, second, third and fourth gas inlet ports in communication with the first, second, third, and fourth gas outlet ports of the first top surface, respectively.

60. A reaction block as in claim 59 wherein the first, second, third and fourth gas inlet ports are in the bottom surface.

61. A reaction block as in claim 60 further including an input port for receiving heating or cooling fluid.

62. A reaction block as in claim 61 wherein the input port for receiving heating or cooling fluid is in the bottom surface.

63. A reaction block as in claim 62 further including an output port for draining heating or cooling fluid.

64. A reaction block as in claim 63 wherein the output port for draining heating or cooling fluid is on the bottom surface.

65. A reaction block as in claim 64 further including a plurality of passages connecting the input port for receiving heating or cooling fluid to the output port for draining heating or cooling fluid.

66. A reaction block as in claim 58 wherein the bottom surface includes a magnet.

67. A reaction block as in claim 66 wherein the magnet is a bar magnet.

68. A reaction block as in claim 58 wherein each of the reaction chambers includes a drain tube.

69. A reaction block as in claim 68 further including a cavity extending upwardly from the bottom surface to a middle surface, the middle surface parallel to the first top surface and the bottom surface.

70. A reaction block as in claim 69 wherein the middle surface has openings for receiving the drain tubes.

71. A reaction block as in claim 70 wherein the cavity includes a machined step to facilitate mating with a microtiter plate.

72. A reaction block as in claim 71 wherein the cavity includes a second machined step to facilitate mating with a bottom seal.

73. A reaction block as in claim 72 wherein the bottom seal includes an o-ring which seals against the second machined step.

74. A reaction block as in claim 72 wherein the bottom seal includes a one-way pressure valve.

75. A reaction block as in claim 59 wherein the first, second, third and fourth gas inlet ports include a quad ring seal.

76. A reaction block comprising:

a plurality of raised beads on a first top surface, the raised beads defining a plurality of chambers;

a plurality of reaction chambers;

a plurality of openings in the first top surface for receiving the reaction chambers; and the first top surface having a gas port and each reaction chamber having a second top surface;

wherein the raised beads and the second top surfaces of the reaction chambers are in the same plane and sealed with means for sealing.

* * * * *